(12) United States Patent
Parida

(10) Patent No.: US 7,925,447 B2
(45) Date of Patent: Apr. 12, 2011

(54) SIGNIFICANCE MEASURE OF STRUCTURED CLUSTERS

(75) Inventor: Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 931 days.

(21) Appl. No.: 11/781,653

(22) Filed: Jul. 23, 2007

(65) Prior Publication Data

US 2009/0030912 A1 Jan. 29, 2009

(51) Int. Cl.
*G06F 19/00* (2011.01)
*G06F 15/00* (2006.01)
*G11C 17/00* (2006.01)
(52) U.S. Cl. ................. 702/20; 365/94; 700/1
(58) Field of Classification Search .......... None
See application file for complete search history.

(56) References Cited

OTHER PUBLICATIONS

Landau et al. Gene Proximity Analysis across Whole Genomes via PQ Trees Journal of Computational Biology, vol. 12, pp. 1289-1306 (2005).*

* cited by examiner

*Primary Examiner* — John S Brusca
(74) *Attorney, Agent, or Firm* — Yee & Associates, P.C.; Anne V. Dougherty

(57) ABSTRACT

The exemplary embodiments provide a computer implemented method, apparatus, and computer usable program code for calculating a probability. An input is received, wherein the input comprises a PQ tree. The leaf nodes of the PQ tree are counted to form a number of leaf nodes. A factorial value of the number of leaf nodes is calculated to form a denominator. A hash value of a frontier of all permutations of the PQ tree is calculated to form a numerator. A ratio of the numerator to the denominator is determined to form a result. The result is displayed to a user.

20 Claims, 6 Drawing Sheets

| interval $[k_1..k_2]$ | | $\Pi(q_1[k_1..k_2])$ | size |
|---|---|---|---|
| 302 ~ [3..4] | 52 \|43\| 1 | {3,4} | 2 |
| 304 ~ [2..4] | 5 \|243\| 1 | {2,3,4} | 3 |
| 306 ~ [1..4] | \|5243\| 1 | {2,3,4,5} | 4 |

*FIG. 3*

$q = 9\ 1\ 5\ 2\ \phi\ 3\ 6\ 4\ 7\ 10\ 8;\ \ -402$

| | |
|---|---|
| 9 1 5 \|2 $\phi$ 3\| 6 4 7 10 8 | 2 |
| 9 1 \|5 2 $\phi$ 3 6 4\| 7 10 8 | 5 |
| 9 \|1 5 2 $\phi$ 3 6 4\| 7 10 8     9 1 \|5 2 $\phi$ 3 6 4 7\| 10 8 | 6(2) |
| \|9 1 5 2 $\phi$ 3 6 4 7 10 8\| | 10 |

| call | u | sig(q) $(k_u)$ | $\Delta_u$ | Case |
|---|---|---|---|---|
| | 10 | (1) | | |
| S(10,2) | 6 | (2) | 3 | 2b |
| | 5 | (1) | | |
| S(5,2) | 2 | (1) | 4 | 1 |
| S(2,2) | – | – | | |

*FIG. 6*

SIGNIFICANCE MEASURE OF STRUCTURED CLUSTERS

BACKGROUND OF THE INVENTION

1. Field of the Invention

The present invention relates generally to data processing systems. More specifically, the present invention is directed to a computer implemented method, system, and computer usable program code for calculating the probability of occurrence of a structured cluster.

2. Description of the Related Art

Consider the scenario, where common gene clusters are extracted from two closely related species such as humans and rats. It is quite possible that in each gene cluster, that there are further clusters within the cluster and so on. One traditional way of computing the probability of the occurrence of a cluster is to ignore the sub-clusters S and simply use the probability of occurrence of each gene in the cluster. The effectiveness of this model is unclear when the number of genes is very large and the number of occurrences of each gene is very small.

SUMMARY OF THE INVENTION

The exemplary embodiments provide a computer implemented method, apparatus, and computer usable program code for calculating a probability. An input is received, wherein the input comprises a PQ tree. The leaf nodes of the PQ tree are counted to form a number of leaf nodes. A factorial value of the number of leaf nodes is calculated to form a denominator. A hash value of a frontier of all permutations of the PQ tree is calculated to form a numerator. A ratio of the numerator to the denominator is determined to form a result. The result is displayed to a user.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 3 illustrates some examples of intervals in accordance with an exemplary embodiment;

FIG. 4 illustrates an arrangement and the intervals included in the arrangement in accordance with an exemplary embodiment;

FIG. 6 illustrates the steps for constructing an arrangement in accordance with an exemplary embodiment;

DETAILED DESCRIPTION OF THE PREFERRED EMBODIMENT

Figure 1:
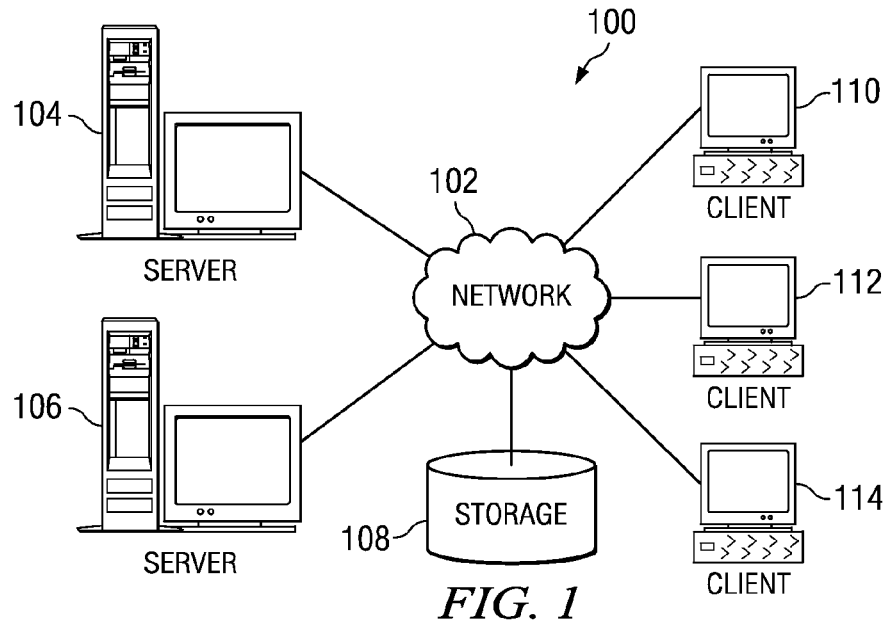
FIG. 1 depicts a pictorial representation of a network of data processing systems in which the illustrative embodiments may be implemented.
Figure 2:
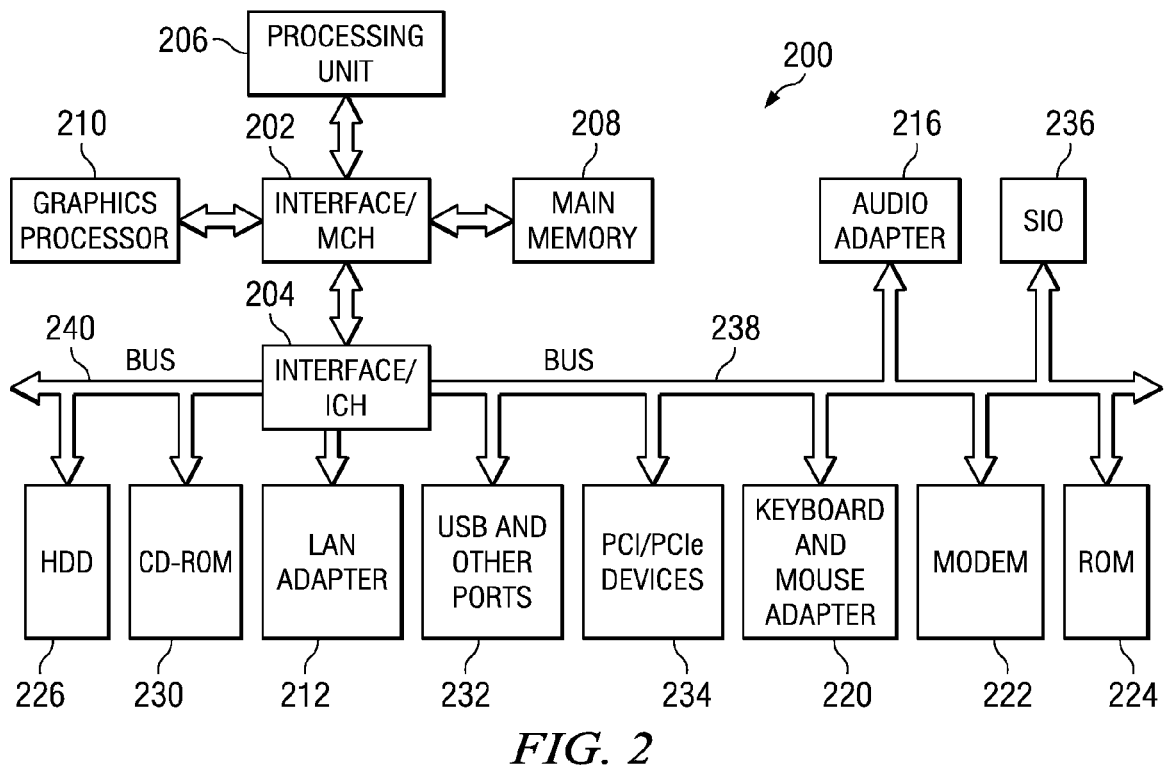
FIG. 2 is a block diagram of a data processing system in which the illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments.

In the depicted example, data processing system 200 employs a hub architecture including interface and memory controller hub (interface/MCH) 202 and interface and input/output (I/O) controller hub (interface/ICH) 204. Processing unit 206, main memory 208, and graphics processor 210 are coupled to interface and memory controller hub 202. Processing unit 206 may contain one or more processors and even may be implemented using one or more heterogeneous processor systems. Graphics processor 210 may be coupled to the interface/MCH through an accelerated graphics port (AGP), for example.

In the depicted example, local area network (LAN) adapter 212 is coupled to interface and I/O controller hub 204 and audio adapter 216, keyboard and mouse adapter 220, modem 222, read only memory (ROM) 224, universal serial bus (USB) and other ports 232, and PCI/PCIe devices 234 are coupled to interface and I/O controller hub 204 through bus 238, and hard disk drive (HDD) 226 and CD-ROM 230 are coupled to interface and I/O controller hub 204 through bus 240. PCI/PCIe devices may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE) or serial advanced technology attachment (SATA) interface. A super I/O (SIO) device 236 may be coupled to interface and I/O controller hub 204.

An operating system runs on processing unit 206 and coordinates and provides control of various components within data processing system 200 in FIG. 2. The operating system may be a commercially available operating system such as Microsoft® Windows Vista™ (Microsoft and Windows Vista are trademarks of Microsoft Corporation in the United States, other countries, or both). An object oriented programming system, such as the Java™ programming system, may run in conjunction with the operating system and provides calls to the operating system from Java™ programs or applications executing on data processing system 200. Java™ and all Java™-based trademarks are trademarks of Sun Microsystems, Inc. in the United States, other countries, or both.

Instructions for the operating system, the object-oriented programming system, and applications or programs are located on storage devices, such as hard disk drive 226, and may be loaded into main memory 208 for execution by processing unit 206. The processes of the illustrative embodiments may be performed by processing unit 206 using computer implemented instructions, which may be located in a memory such as, for example, main memory 208, read only memory 224, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course, the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache such as found in interface and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

Consider the scenario where common gene clusters are extracted from two closely related species such as humans and rats. It is quite possible that in each gene cluster, there are further clusters within the cluster and so on. Therefore, let the collection of all possible 'sub'-clusters within this common cluster that occur in both the species be denoted by S.

Exemplary embodiments address such a scenario by not using the probability of occurrence of each individual gene, but assigning a conditional probability to the sub-clusters S, given the occurrence of the cluster. This is a better estimate of the probability of the cluster due to, for instance, an improvement in sensitivity since it can be used to compare the statistical significance of gene clusters of the same sizes, which under the traditional model would give identical probabilities, assuming identical probabilities for all the genes.

The collection of sub-clusters S has an elegant form that can be captured as a nested structure, or a PQ tree, which is a data structure that was originally used to efficiently solve a combinatorial problem called the consecutive ones problem. A nested structure is a structure that contains sub-clusters within clusters, wherein some sub-clusters may overlap each other.

A tree is a cyclic graph where every node, except the root node, has an ancestor or parent node and possible multiple child nodes or children. A root node has no ancestors or parents, only children. A leaf node is a node that does not have any children. A PQ tree is a rooted tree whose internal nodes are of two types: P and Q. A P-node is a node in which the children of the node occur in no particular order. A Q-node is a node in which the children of the node appear either in a left to right order or in a right to left order. Within the disclosure, a P-node is designated by a circle, and a Q-node is designated by a rectangle. Such sub-clusters are sometimes referred to as maximal permutation patterns or maximal clusters.

Exemplary embodiments address the problem:
Given n random permutations of k, what is the probability that K of the n permutations have the sub-clusters given as S?

One particular application of this problem is in the area of genetics. In such a case, the permutations would be permutations of contiguous genes on chromosomes and k would be k genes. Contiguous genes or objects are genes or objects that are adjacent to one another or are ordered one after the other, without any other such object or gene in between them. Exemplary embodiments provide a solution that gives a time to solve this problem exactly, which in a worst-case is a polynomial (quadratic) time.

A cluster is a collection of genes, S, that occurs multiple times, say K times, in a contiguous fashion in the input data, which, for example, could be gene orders in chromosomes of n different organisms. A structured cluster is a conveniently annotated cluster that identifies all of its sub-clusters that appear within the cluster in all its K occurrences. A structured cluster is also sometimes called a maximal cluster. Structured clusters have a PQ tree structure.

Thus, the next step is to examine the PQ tree structure. Let a sequence s be defined on some finite alphabet $\Sigma$. A finite alphabet is an alphabet that has a limit to its size; the alphabet is not infinite in size. A finite alphabet is used to represent some finite set of things or objects, which could be, for example, genes or chromosomes or leaves on a tree. Define $$\Pi(s[i_1 \ldots i_2]) = \{s[i] | i_1 \leq i \leq i_2\}.$$

A permutation, q, on Σ respects cluster constraints S⊂Σ if there exists some $1 \leq i_1 \leq i_2 \leq n$ such that $$S = \Pi(q[i_1 \ldots i_2]).$$

In other words, the elements of S appear together (in any arbitrary order) in q. Let $$\Sigma = \{1, 2, \ldots, n\}.$$

Consider $$S = \{S_1, S_2, \ldots, S_N\},$$

where for $1 \leq i \leq N$, $$S_i \subset \Sigma.$$

Thus, a permutation, q, on Σ satisfies the cluster constraints S, if it respects each cluster constraint $S_i \in S$. A constraint is a condition. A cluster constraint is therefore, a condition imposed on the cluster. In the present example, the specific cluster constraint is that every element of the cluster needs to be contiguous. Clearly, it is quite possible that such a permutation q may not exist for some S. For example, there is no q that respects $$S = \{\{1,2\}, \{2,3\}, \{1,3\}\}.$$

Then, the question arises, is there a way to determine if there exists some q that satisfies the cluster constraints S? This very same problem is addressed by the classical combinatorial problem, the general consecutive arrangement problem, which is stated as follows: "Given a finite set Σ and a collection S of subsets of Σ, does there exist a permutation π of Σ in which the members of each subset $S \subset S$ appear as a consecutive substring of π?"

The leaves of PQ tree T are labeled bijectively by the elements of Σ. Bijectively labeled means each element of a cluster is assigned to a unique leaf node and every element is assigned to a leaf node. This produces a one to one mapping. Thus, if something is labeled bijectively, there is not multiple assignment of the leaves nor is there multiple assignment of the elements of the cluster. The frontier of tree T, denoted by the designation F(T), is the permutation of Σ obtained by reading the labels of the leaves of tree T from left to right.

Two PQ trees T and T' are equivalent, which is denoted as T≡T' if one can be obtained from the other by applying a sequence of the following transformation rules: (1) Arbitrarily permute the children of a P-node, and (2) Reverse the children of a Q-node.

Any frontier obtainable from a tree that is equivalent with tree T is considered consistent with T and Fr(T) is defined as follows:

$$Fr(T) = \{F(T') | T' \equiv T\}.$$

Thus, a PQ tree T captures all the sub-clusters in a cluster of genes. Fr(T) stands for the frontier of all possible permutations of T, where as F(T) stands for the single frontier of T.

To summarize, if T is a PQ tree with k leaf nodes labeled by k integers, $\Sigma = 1, 2, \ldots, k$, then this tree T 1. has k leaf nodes, and,
2. has N internal nodes (some P-nodes and some Q-nodes), with N<k.

The prior art addresses the question of: Given n random permutations of k genes, what is the probability that K of the n permutations have the cluster S?

In this question, any sub-clusters that the K occurrences of S may display are not of interest. However, consider a scenario where an element of an alphabet occurs only a few times but the size of the alphabet is relatively large.

Since a cluster or a permutation pattern can be hierarchically structured as a PQ tree, it is meaningful to ask: Given a permutation pattern q, where $q = \{\sigma_1, \sigma_2, \ldots, \sigma_l\}$, that occurs K times in the input, what is the probability, pr(T,K), of its maximal form given as a PQ tree T?

Assume that the probability of occurrence of each individual element, in the case of the examples, genes, is identical and independent. The probability of occurrence of each individual element is computed using |Fr(T)| for a given PQ tree T. The "||" symbol stands for the number of elements in the set. Thus |Fr(T)| stands for the number of elements in the set Fr(T).

An arrangement of size k is defined to be a permutation, or string, of k consecutive integers. For example, $q_1$ and $q_2$ are arrangements of sizes 5 and 3 respectively:

$$q_1 = 5\ 2\ 4\ 3\ 1,$$

$$q_2 = 4\ 5\ 6.$$

Also, let $\Pi (q[k_1 \ldots k_2]) = \{q[k] | k_1 \leq k \leq k_2\}$. Thus, $$\Pi(q_1[1 \ldots 5]) = \{1,2,3,4,5\}$$

$$\Pi(q_2[1 \ldots 3]) = \{4,5,6\}.$$

Let q be an arrangement of size k, then $[k_1 \ldots k_2]$, $1 \leq k_1 \leq k_2 \leq k$, is an interval in q if for some integers i<j, the following holds:

$$\Pi(q[k_1 \ldots k_2]) = \{i, i+1, i+2, \ldots, j\}.$$

Note that [1 . . . k] is always an interval, hence, it is called the trivial interval. Every other interval is non-trivial. A non-trivial interval is any interval other than a trivial interval.

Turning back to the figures, FIG. 3 illustrates some examples of intervals. FIG. 3 shows three examples of intervals, intervals 302, 304 and 306. Each interval contains a non-trivial interval. Interval 302 includes non-trivial interval 4, 3. Interval 304 includes non-trivial interval 2, 4, 3. Interval 306 includes non-trivial interval 5, 2, 4, 3.

A P-arrangement is an arrangement that does not have any non-trivial arrangements. For example, $q_1$ and $q_2$ are not P-arrangements but $q_3$ and $q_4$ are where $q_3 = 1\ 2$, and $q_4 = 2\ 4\ 1\ 3$.

Next, the number of P-arrangements of size k needs to be determined. Thus, the following assumptions are made. Let q be a P-arrangement of size k+1. Let q be obtained by replacing an extreme element from its position j in q, with the empty symbol. Then q' is a P-arrangement for every interval $[i_1 \ldots i_2]$ in q' such that $i_2 < j < i_2$. An extreme element is either k+1 or 1.

Now, let q be an arrangement obtained by augmenting an arrangement of size k with symbol φ in position j. Further, assume all the intervals $[i_1 \ldots i_2]$ are such that $i_1 < j < i_2$. Such an arrangement is called a nested arrangement. A nested arrangement is an arrangement where all the intervals $[i_1 \ldots i_2]$ are such that $i_1 < j < i_2$. For example, let q be an arrangement of size 10, with j being the fifth element. Thus, the arrangement would look like:

$$q = 9\ 1\ 5\ 2\ \phi\ 6\ 4\ 7\ 10\ 8,$$

Turning back to the figures, FIG. 4 illustrates an arrangement and the intervals included in the arrangement. Arrangement 402 is q=9 1 5 2 φ 3 6 4 7 10 8. This arrangement includes five intervals, which are shown by reproducing the arrangement for each interval and enclosing the intervals in boxes. The size of the intervals is shown to the right of each arrangement.

As can be seen in FIG. 4, arrangement 402 contains five total intervals with four different lengths, there being two intervals of length six.

Arrangement 402 actually has a seventh interval of length 7. However, as explained later, there is a rule that states that if you have two intervals of length k+1, then there must be one interval of length k+1. Thus, the fact that that arrangement 402 contains two intervals of length six also denotes that the arrangement contains an interval of length 7. Thus, there is no need to include this information in the signature.

A signature for a nested arrangement is the ordered list of all the interval sizes of the nested arrangement. The number of intervals of the same size is indicated in brackets as shown in the following example. Thus, for the example arrangement presented in FIG. 4, the signature of q would be given as:

$$sig(q)=2(1)<5(1)<6(2)<10(1).$$

In the exemplary embodiment presented in FIG. 4, the empty symbol $\phi$ was explicitly introduced in position j of the arrangement. However, one skilled in the art can see that in alternate embodiments the nested arrangement can also be defined without this by simply identifying a pair of positions $i_1$ and $i_2$ in the arrangement, instead of j. For example, in an alternate embodiment, arrangement 402 in FIG. 4 could be presented as:

$$q=9\ 1\ 5\ 2\ \underline{3}\ 6\ 4\ 7\ 10\ 8,$$

with the positions $i_1=4$ and $i_2=5$.

Thus, the problem of enumerating all the arrangements with a given signature arises. Exemplary embodiments address this problem by providing a process called inverse-telescoping. Inverse-telescoping is the process of replacing an element of an arrangement q with another arrangement and appropriately renumbering the elements of q. What it means to renumber appropriately is explained in greater detail in the following nineteen paragraphs.

The following is an example of inverse-telescoping. Let q=1 2 3 where the element 2 is inverse-telescoped with the arrangement 2 4 3 to obtain q'. Note that element 3 of q has to be renumbered to 5 in q'. Thus $$q' = 1\,(2\,4\,3)\,3$$
$$= 1\,2\,4\,3\,5.$$

In the case of a P-arrangement of size k, if the element i in q is to be inverse-telescoped, there are two possible options.

In the first option, element i is inverse-telescoped with a P-arrangement of $$i, i+1, \ldots, i+k-2, i+k-1,$$

and the elements i+1 or more of q are each renumbered accordingly, that is increased by k-1, as shown in the following example.

For example, let q=1 2 with k=4 and i=1. Then:

1 2 $\Rightarrow$(2 4 1 3)2 (element 1 of q inverse-telescoped)

$\Rightarrow$2 4 1 3 5. (element 2 of q renumbered)

In the second option, element i is inverse-telescoped with a P-arrangement of $$i-k+1, i-k+2 \ldots, i-1, i,$$

and the elements of q, i−1 or less, are each renumbered accordingly, that is, decreased by k−1. Then all the elements of this new arrangement may be increased to have only positive integers as elements of the arrangement.

For example, let q=1 2 with k=4 and i=1. Then 1 2 $\Rightarrow$(0 −2 1 −1)2 (element 1 of q inverse-telescoped)

$\Rightarrow$3 1 4 2 5. (all elements increased by 3)

In order to maintain consistency and for simplicity of explanation, only one option, the first option will be used throughout the remainder of the disclosure. However, it should be understood that alternate embodiments contemplate the use of the second option. The limiting of the discussion to the first option in no way limits the disclosure to only the first option. Further the second option may be applied to any examples and achieve the same end result. Discussion of the second option is simply omitted to avoid overly repetitive discussion.

Figure 5:
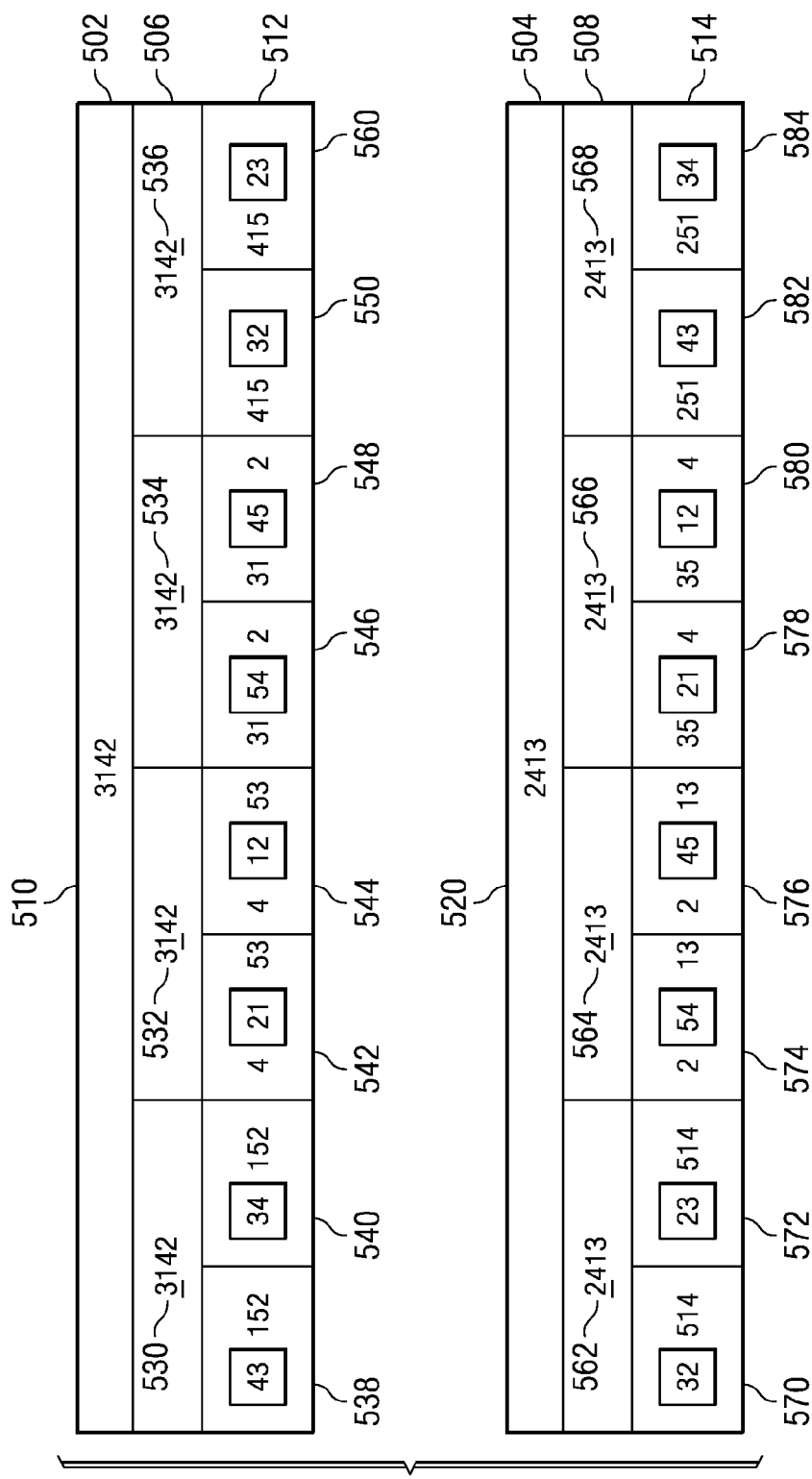
FIG. 5 illustrates the enumeration of the arrangements corresponding to signature 2(1)<5(1) in accordance with an exemplary embodiment.

Turning back to the figures, FIG. 5 illustrates the enumeration of the arrangements corresponding to signature 2(1)<5(1) in accordance with an exemplary embodiment. The smallest interval is of size 2 and the next, and the largest, interval is of size 5. Thus, the arrangement must be of size 5.

Therefore, consider all P-arrangements of size 5−2+1=4. These two P-arrangements are shown in P-arrangement 510, which is in row 502 and P-arrangement 520, which is row 504. Then, each element of P-arrangements 510 and 520 is inverse-telescoped—telescoped with a P-arrangement of size 2. Row 506 comprises 4 cells, each of which contains P-arrangement 510 but with a different element of P-arrangement 510 underlined in each column. The underlined element is the element that will be replaced by the P-arrangement of size 2, as shown in the corresponding cells of row 512. Row 508 comprises 4 cells, each of which contains P-arrangement 520 but with a different element of P-arrangement 520 underlined in each column. The underlined element is the element that will be replaced by the P-arrangement of size 2, as shown in the corresponding cells of row 514. The substituted P-arrangement of size 2 is illustrated in each cell by a square that encloses the elements.

Thus cell 530 shows P-arrangement 510 with the first element, 3, underlined. Cells 538 and 540 show P-arrangement 510 after the first element, 3, has been inverse-telescoped with a P-arrangement of size 2 and renumbered. Thus, cell 538 shows an arrangement of 43152, while cell 540 shows an arrangement of 34152.

Cell 532 shows P-arrangement 510 with the second element, 1, underlined. Cells 542 and 544 show P-arrangement 510 after the second element, 1, has been inverse-telescoped with a P-arrangement of size 2 and renumbered. Thus, cell 542 shows an arrangement of 42152, while cell 544 shows an arrangement of 41253.

Cell 534 shows P-arrangement 510 with the third element, 4, underlined. Cells 546 and 548 show P-arrangement 510 after the third element, 4, has been inverse-telescoped with a P-arrangement of size 2 and renumbered. Thus, cell 546 shows an arrangement of 31542, while cell 548 shows an arrangement of 31452.

Cell 536 shows P-arrangement 510 with the fourth element, 2, underlined. Cells 550 and 560 show P-arrangement 510 after the fourth element, 2, has been inverse-telescoped with a P-arrangement of size 2 and renumbered. Thus, cell 550 shows an arrangement of 41532, while cell 560 shows an arrangement of 41523.

Cell 562 shows P-arrangement 520 with the first element, 2, underlined. Cells 570 and 572 show P-arrangement 520 after the first element, 2, has been inverse-telescoped with a P-arrangement of size 2 and renumbered. Thus, cell 570 shows an arrangement of 32514, while cell 572 shows an arrangement of 23514.

Cell 564 shows P-arrangement 520 with the second element, 4, underlined. Cells 574 and 576 show P-arrangement 520 after the second element, 4, has been inverse-telescoped with a P-arrangement of size 2 and renumbered. Thus, cell 574 shows an arrangement of 25413, while cell 576 shows an arrangement of 24513.

Cell 566 shows P-arrangement 520 with the third element, 1, underlined. Cells 578 and 580 show P-arrangement 520 after the third element, 1, has been inverse-telescoped with a P-arrangement of size 2 and renumbered. Thus, cell 578 shows an arrangement of 35214, while cell 580 shows an arrangement of 35124.

Cell 568 shows P-arrangement 520 with the fourth element, 3, underlined. Cells 582 and 584 show P-arrangement 520 after the fourth element, 3, has been inverse-telescoped with a P-arrangement of size 2 and renumbered. Thus, cell 582 shows an arrangement of 25143, while cell 584 shows an arrangement of 25134.

The results shown in FIG. 5 also suggests a method for a systematic enumeration by successive inverse-telescoping. This method is useful in evaluating the function S(u, l), which counts all the nested arrangements whose signature is of the form $$l(\bullet) < \ldots < u(1)$$

In the example shown in FIG. 5, l(•) is either l(1) or l(2) and the number of the non-trivial intervals is not known. It is possible that l=u.

Exemplary embodiments provide for counting, as well as enumerating, all P-arrangements of size k. The first step is to count or enumerate all nested arrangements of size k−1.

The following functions are used to estimate the number of P-arrangements. Function Pa(k) calculates the number of P-arrangements of size k. Function S(u, l), calculates the number of nested arrangements of size u with the smallest interval having a size of l. Function $S_{cnt}(u, l)$ calculates the number of nested arrangements wherein the highest valued element occurs in the smallest interval, which has a size of l. Functions Nst(k) and Nst'(k) count all possible nested arrangements of size k by accounting for all possible values of the smallest interval size l.

The counting method involves enumerating all possible signatures for a fixed size of the arrangement and for each signature, enumerating all possible arrangements. Exemplary embodiments provide a recursive formulation to address this problem.

Previously, the signature for a nested arrangement has been defined in terms of the sizes of the intervals in the arrangement. Thus, it may be concluded that a nested arrangement has a unique signature. However, multiple arrangements may have the same signature.

It is possible that two intervals in a nested arrangement may straddle. Straddle means that the two intervals have a common intersection and neither of the two intervals is a subset of the other interval. Furthermore, if two intervals straddle, then they must be of the same size, say k', and they must overlap in k'−1 positions. In other words, the two intervals have an intersection of size k'−1, which in turn is also an interval. Thus, one may conclude, based on the definitions of nested arrangements and intervals, that there is only one interval of the smallest size l and that the number of intervals of a fixed size k' can be no more than 2.

All the preceding observations are summarized in the following lemma. A lemma is a supporting theorem.

Lemma 1 (signature lemma) Let q be an arrangement of size k with symbol φ in position j with all the intervals [$i_{l1} \ldots i_{l2}$] satisfying $$i_{r1} < j < i_{r2},$$

for all $1 \leq r \leq K$. Let the size of the interval be $i_r = i_{r2} - i_{r1} + 1$.

Further if two straddling intervals, where one is not nested in the other, are of size i and i', then i=i' and they must overlap in i−1 positions.

A consequence of this is that the signature $$sig(q) = i_1(k_{i1}) < i_2(k_{i2}) < \ldots < i_r(k_{ir}) < \ldots < i_K(k_{iK}),$$

is unique with $k_1=1$, $k_K=1$, $i_K=k$, and each $k_r$, $1 \leq r < K$, is either 1 or 2.

To avoid clutter, if $k_r=1$, it is omitted. For example, if $$sig(q) = 4 < 5(2) < 6 < 7 < 8 < 9 < 10$$

then, using this convention, a formula for the function S(u, l) is obtained.

The function S(u, l), where $u \geq l > 1$, is the number of nested arrangements of size u where the smallest interval is of size l. Of these nested arrangements, the function $S_{cnt}(u, l)$ is the number of arrangements where the highest valued element occurs in the smallest interval, l.

Based on the lemma, a formula for S(u, l) may be obtained. Pa(Δ) is the number of P-arrangements of size Δ. Then, from the definition, it follows that $$S(l,l) = Pa(l).$$

Exemplary embodiments use a recursive formula to generate an arrangement given a signature. Thus, for a nested arrangement of size u, the size of the largest interval x (but smaller than u) can be expressed as $$u-1, u-2, u-3, \ldots, l+1, l.$$

where l is the size of the smallest interval.

By treating the interval of size x as a single element, the arrangement of size u can actually be viewed as a P-arrangement of size u−x+1, called $\Delta_x$. The number of such arrangements is Pa($\Delta_x$) and $\Delta_x > 1$.

If the P-arrangements are such that an extreme element does not occur at the end positions, then there is clearly no problem in generating non-trivial intervals in the inverse-telescoping process. Thus, when $\Delta_x > 3$, Pa($\Delta_x$) can be used recursively. Also when $\Delta_x = 3$, Pa($\Delta_x$)=0. Also, if element i is being inverse-telescoped, then if its existing neighbor cannot be i+1 and if the neighbor is i+2, the neighbor will be renumbered to i+3. Thus, there is no problem with inverse-telescoping with an interval of size 2.

Next, consider the scenario where intervals are not strictly nested. It has already been shown that, at most, two intervals of the same size, x, may straddle. Further it has been shown that when two intervals straddle, that there is also always an interval of size x−1. Thus, this triple of intervals can be tracked simultaneously, which corresponds to Case 2b, which is discussed below. Furthermore, multiple intervals of the same size can be dealt with just one factor in the formula for S(u, l).

Case 1 ($\Delta_x > 3$ or $x < u-2$): Any one element of these $\Delta_x$ elements can be picked to be the interval of size x and each interval of size x can have S(x, l) arrangements, giving $\Delta_x S(x, l)$ possibilities. Thus, the total number of arrangements is:

$$Pa(\Delta_x) \Delta_x S(x,l)$$

Case 2a ($\Delta_x = 2$ or $x = u-1$) and Case 2b ($\Delta_x = 3$ or u−2): This scenario can be understood by considering all the possible arrangements of size 3. The boxed numbers corresponds to the interval of size x, which is being treated as a single element. Also, $k_x$ denotes the number of intervals of size x.

| arrangements | | | | $k_x$ |
|---|---|---|---|---|
| | | Case 2a | | |
| 1 [3 2] | 2 3] 1 | | $\Delta_x = 2$ or $x = u-1$ | 1 |
| [2 1] 3 | 3 [1 2] | | $\Delta_x = 2$ or $x = u-1$ | 1 |
| | | Case 2b | | |
| 1 [2] 3 | 3 [2] 1 | | $\Delta_x = 3$ or $x = u-2$ | 2 |

Now, the exact form of S(u, l) may be obtained. Let
$\Delta_x = u-x+1$.
Then $$S(u, l) = \begin{array}{l} 4S(u-1, l) \\ + 2S(u-2, l) \\ + \Delta_{u-3}Pa(\Delta_{u-3})S(u-3, l) \\ + \Delta_{u-4}Pa(\Delta_{u-4})S(u-4, l) \\ \vdots \\ + \Delta_l Pa(\Delta_l)S(l, l) \end{array} \begin{array}{l} \Delta_{u-1} = 2 \\ \Delta_{u-2} = 3 \\ \Delta_{u-3} = 4 \\ \Delta_{u-4} = 5 \\ \vdots \\ \Delta_{u-(u-l)} = u-l+1 \end{array} \begin{array}{l} (k_{u-1} = 1) \\ (k_{u-2} = 2, 1) \\ (k_{u-3} = 1) \\ (k_{u-4} = 1) \\ \vdots \\ (k_l = 1) \end{array} \begin{array}{l} \text{(Case 2a)} \\ \text{(Case 2b)} \\ \text{(Case 1)} \\ \text{(Case 1)} \\ \\ \text{(Case 1)} \end{array}$$

Thus $$S(u, l) = 4S(u-1, l) + 2S(u-2, l) + \sum_{y=3}^{u-l} \Delta_{u-y} Pa(\Delta_{u-y}) S(u-y, l).$$

Case 1 corresponds to the third term, $\Sigma \Delta_{u-y} Pa(\Delta_{u-y}) S(u-y, l)$, of S(u, l). Case 2a corresponds to the first term, 4S(u-1, l), of S(u, l). Case 2b corresponds to the second term, 2S(u-2, l), of S(u, l).

The formula for S(u, l) can be used both for counting as well as enumerating.

FIG. 6 illustrates the steps for constructing an arrangement in accordance with an exemplary embodiment. Consider the arrangement presented in FIG. 4, arrangement 402, without the empty symbol:

q=9 1 5 2 3 6 4 7 10 8

FIG. 6 illustrates the steps for constructing an arrangement using the formula for S(u, l). In this case, u=10, l=2. The formula is a recursive formula, thus making the first call of (10, 2), as shown in column 1, entitled call, will cause the other two calls shown to be made. Columns 2 and 3 show the corresponding u and $k_u$ values for the call made in column 1. Columns 4 and 5 simply explain what is happening in columns 1 through 3. That is for the first call, $\Delta u$ is 3 and this corresponds to Case 2b.

Constructing $S_{cnt}$(u, l) follows easily based on S(u, l). $S_{cnt}$(u, l) is the count of arrangements where the largest element, u in this case, is in the smallest interval of size l. Following the convention of the inverse-telescope process, only the highest valued element needs to be tracked at each recursion. The first two rows below illustrate checking the case of $\Delta_x$<3. In the remaining rows, the factor $\Delta_x$ is removed from each term, since only one of these will be the highest value.

$$S_{cnt}(u, l) = \begin{array}{l} 2S_{cnt}(u-1, l) \\ + 0S_{cnt}(u-2, l) \\ + Pa(\Delta_{u-3})S_{cnt}(u-3, l) \\ + Pa(\Delta_{u-4})S_{cnt}(u-4, l) \\ \vdots \\ + Pa(\Delta_l)S_{cnt}(l, l) \end{array} \begin{array}{l} \Delta_{u-1} = 2 \\ \Delta_{u-2} = 3 \\ \Delta_{u-3} = 4 \\ \Delta_{u-4} = 5 \\ \vdots \\ \Delta_{u-(u-l)} = u-l+1 \end{array} \begin{array}{l} (k_{u-1} = 1) \\ (k_{u-2} = 2, 1) \\ (k_{u-3} = 1) \\ (k_{u-4} = 1) \\ \\ (k_l = 1) \end{array}$$

Then $$S_{cnt}(u, l) = 2S_{cnt}(u-1, l) + \sum_{y=3}^{u-l} Pa(\Delta_{u-y}) S_{cnt}(u-y, l).$$

Thus, the number of arrangements of size u with the largest element not on the smallest interval of size l can be expressed as:

$S(u,l) - S_{cnt}(u,l)$.

As Nst(k) is the number of nested arrangements of size k, it follows that Nst(k) can be defined in terms of S(•, •) as follows:

$$Nst(k) = \sum_{l=2}^{k} S(k, l).$$

However, it is also desirable to count the number of potential places in the arrangements where element k+1 can be inserted. The positions are all in the smallest interval of size l. The number of positions that the element k+1 can be inserted in the arrangement is denoted as Nst'(k).

For a fixed u and l, (a) the number of nested arrangements where the largest element is in the smallest interval is $S_{cnt}$(u, l); and (b) the number of nested arrangements where the largest element is not in the smallest interval is S(u, l)−$S_{cnt}$(u, l). Therefore, when l=2, the element k+1 can be inserted in the nested P-arrangement only if the largest element is not in the smallest interval. This scenario is referred to as Case A. The number of arrangements in Case A may be expressed as:

S(k,2)−$S_{cnt}$(k,2)

When l>3, then there are two possible scenarios, referred to as Case B and Case C.

In Case B, the largest element k is in the smallest interval of size l. Clearly, k+1 cannot be inserted next to the element k in the interval. Thus element k+1 has a possible l minus 3 (l−3) positions where element k+1 can be inserted, giving a count of (l−3)$S_{cnt}$(k,l).

In Case C, the largest element k is not in the smallest interval of size l. Clearly, k+1 can be inserted at any position in the interval giving a count of $$(l-1)(S(k,l)-S_{cnt}(k,l)).$$

Then $$Nst'(k) = S(k, 2) - S_{cnt}(k, 2) + \quad \text{(Case A)}$$

$$\sum_{l=4}^{k}(l-3)S_{cnt}(k, l) + \quad \text{(Case B)}$$

$$\sum_{l=4}^{k}(l-1)(S(k, l) - S_{cnt}(k, l)) \quad \text{(Case C)}$$

Where line 1 of the formula refers to Case A, line 2 of the formula refers to Case B and line 3 of the formula refers to Case 6.

Thus, $$Nst'(k) = S(k, 2) - S_{cnt}(k, 2) + \sum_{l=4}^{k}(l-1)S(k, l) - 2S_{cnt}(k, l).$$

Thus, based on the following assumptions: (i) let q be a P-arrangement of size k+1; (ii) let q be obtained by replacing an extreme element, either k+1 or 1, from its position j in q, with the empty symbol; and (iii) then q' is a P-arrangement for every interval $[i_1 \ldots i_2]$ in q' such that $i_1 < j < i_2$; it follows that:

$$Pa(2)=2,$$

$$Pa(3)=0,$$

$$Pa(4)=2,$$

$$Pa(k)=Nst'(k-1), \text{ for } k>4.$$

Figure 8:
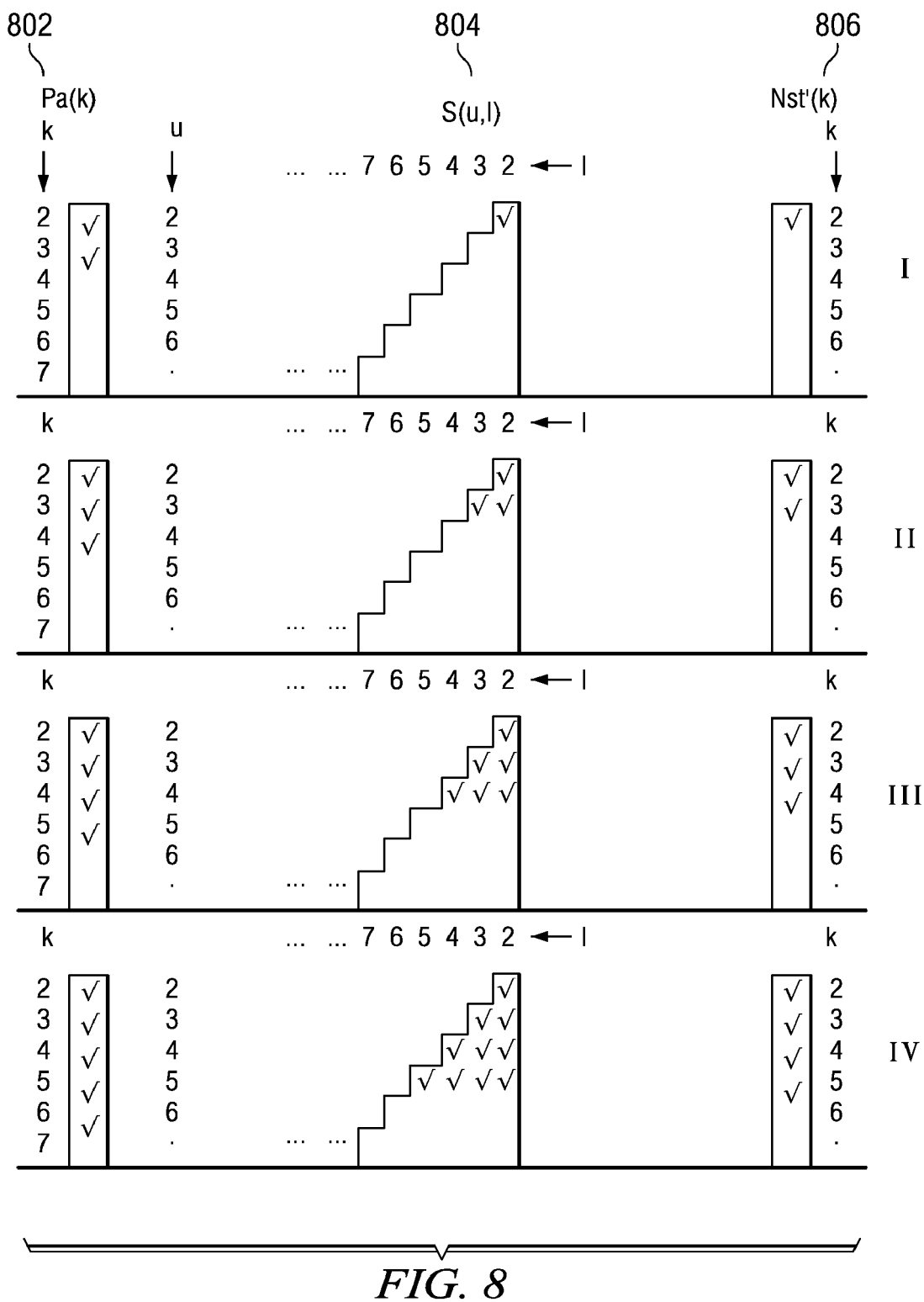
FIG. 8 illustrates evaluating Pa(•),S(•,•), and Nst'(•) functions using dynamic programming in accordance with an exemplary embodiment.

Note that Pa(•) is defined in terms of Nst'(•), which is defined in terms of S(•, •) which is again defined in terms of Pa(•). However, the dependence is such that exemplary embodiments use dynamic programming to evaluate the functions, as shown in FIG. 8.

A lower bound on Pa(k) or an underestimate of the number of P-arrangements can be obtained by only using l=k. In other words, if the task is to count P-arrangements of size k, k-1 can be used for each element of k. However, this solution is not complete because some arrangements of k cannot be determined this way. This is achieved by using the following recurrence equations:

$$Pa(2)=2,$$

$$Pa(3)=0,$$

$$Pa(4)=2,$$

$$Pa(k) \geq (k-4)Pa(k-1), \text{ for } k>4.$$

Solving this Recurrence Form Gives $$Pa(k) \geq 2(k-4)!, \text{ for } k \geq 4.$$

Note that q', the inversion of a P-arrangement q, is also a P-arrangement. Thus, q' can be constructed by inverting q. This points to another question, given a P-arrangement q, what are the other P-arrangements, that can be constructed trivially from q? These arrangements are referred to as isomorphic P-arrangements. An isomorphic P-arrangement is an arrangement that can be constructed easily, like inverting, from another arrangement.

Let q be an arrangement of size k. The operators inverse(q) and reserve(q) are defined using the following example for q:

$$q=2\ 4\ 1\ 5\ 3.$$

Thus, for $1 \leq i \leq k$, q'=inverse(q) is defined as follows: q'[i]←q[k−i+1]. Thus, inverse(2 4 1 5 3)=3 5 1 4 2.

Also, for $1 \leq i \leq k$, q'=reverse(q) is defined as follows: q'[i]←k−q[i]+1. Thus, reverse(2 4 1 5 3)=4 2 5 1 3.

Note that for q=2 4 1 3, inverse(q)=reverse(q)=3 1 4 2. Also, the two operators can be combined as follows: inverse(reverse(2 4 1 5 3))=inverse(4 2 5 1 3)=3 1 5 2 4.

Lemma 2: The two operators commute, i.e., given q, an arrangement of size k,
inverse(reverse(q))=reverse(inverse(q)).

Lemma 3, isomorphic lemma: If q is a P-arrangement of size k, then inverse(q) and reverse(q) are also P-arrangements of size k.

Thus, it follows that inverse(reverse(q)) is also a P-arrangement of size k.

Given a PQ tree T with k leaf nodes, what is the size of the frontier set Fr(T)? In other words, what is the number of arrangements that encode exactly the same subsets of Σ as T?

The formula for computing the size of Fr(T) using the function Pa(•) is as follows.

We define #(A), for each node A of T as follows. #(A) stands for the hash of A. Let node A in the PQ tree T have c children $A_1, A_2, \ldots, A_c$. Then $$\#(A) = \begin{cases} 1 & \text{if } A \text{ is a leaf node,} \\ 2\prod_{j=1}^{c} \#(A_j) & \text{if } A \text{ is a } Q \text{ node,} \\ Pa(c)\prod_{j=1}^{c} \#(A_j) & \text{if } A \text{ is a } P \text{ node.} \end{cases}$$

The symbol Π stands for multiplication. Thus, in order to calculate the hash of A, a user adds the total of all calculations performed according to the right hand side of the formula above. From this it follows that:

$$\#(\text{Root}(T))=|Fr(T)|.$$

where Root(T) is the root node of the PQ tree T. FIGS. 7A-E provide an example of this.

Figure 7A:
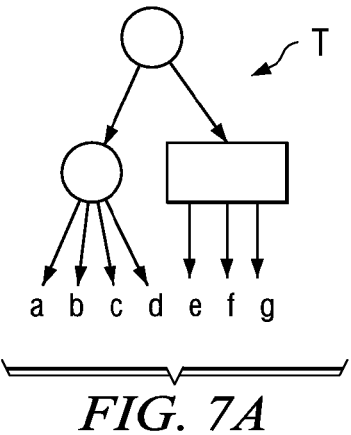
FIGS. 7A-7E illustrate estimating the size of a frontier set in accordance with an exemplary embodiment.

FIGS. 7A-E illustrate estimating the size of a frontier set, in accordance with an exemplary embodiment. FIG. 7A shows a blank input PQ tree T. PQ Tree T includes seven (7) leaf nodes, a though g, in this example. P-nodes are shown by circles, of which there are 2, and Q-nodes are shown by rectangles, of which there is one. However, PQ tree T could include any number of leaf nodes, P-nodes, and Q-nodes. The present example is for explanatory purposes only and is not intended to in any way limit alternate embodiments to only the example embodiment shown.

Figure 7B:
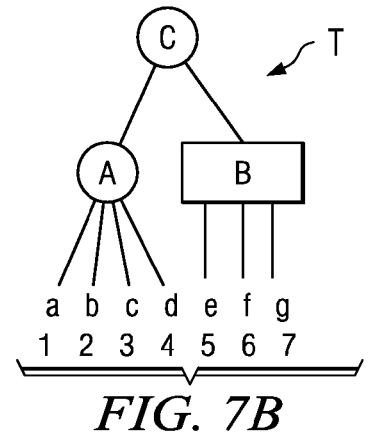

FIG. 7B shows PQ Tree T with leaf nodes, P-nodes, and Q-nodes labeled. The leaf nodes a through g are numbered from left to right, 1 through 7. The two P-nodes are labeled A and C. The Q-node is labeled B.

Figure 7C:
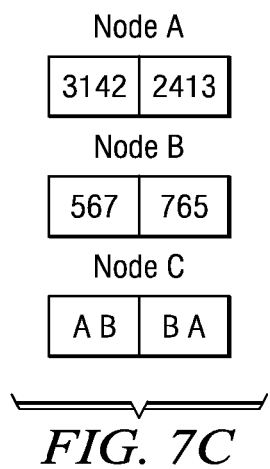
Figure 7D:
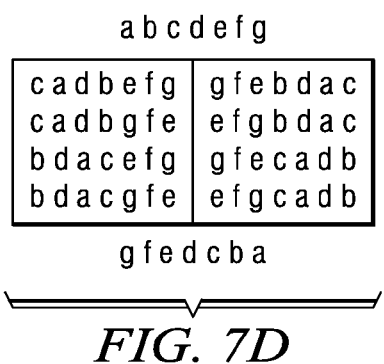

FIG. 7C shows the possible arrangements for each node. FIG. 7D shows the ten (10) possible arrangements for the entire PQ tree T. The arrangements 1 2 3 4 5 6 7 and its inversion 7 6 5 4 3 2 1, are clearly frontiers. The other arrangements are computed as follows. For each P node of T with c children, Pa(c) gives the number of possible arrangements of the children. For each Q-node, the number of possible arrangements is only two.

Figure 7E:
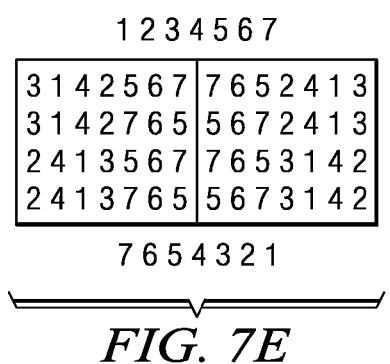

FIG. 7E illustrates the same ten (10) possible arrangements shown in FIG. 7D, except the arrangements are labeled according to the input alphabet rather than numerically.

Compatibility is defined as follows. Let q be a permutation of some finite set Σ and let T be a PQ tree with its leaf nodes labeled by elements of Σ. Further, let q be of size |Σ| and let T have |Σ|leaf nodes. Then T is compatible with q and vice-versa, if and only if q is a frontier of T or q∈Fr(T).

Again, examine the question "What is the probability, pr(T), of a PQ tree T which has n leaf nodes, labeled by integers 1, 2, . . . , n, being compatible with a random permutation of 1, 2, . . . , n?"

Note that n↓ is the total number of permutations of length n. Then, the probability is given as $$pr(T) = \frac{|Fr(T)|}{n!}$$

Alternative embodiments reach the same conclusion though a different path. Let T be a tree with n leaf nodes. The leaf nodes are labeled by integers 1, 2, . . . , n in the left to right order. Let q be a random permutation of integers 1, 2, . . . , n. Then the probability, pr(T), of the occurrence of the event q∈Fr(T) is given by $$pr(T) = \frac{|Fr(T)|}{n!}$$

Thus, both paths lead to the same conclusion. Further it should be noted that in other alternate embodiments, the leaf nodes of T may be labeled in any order, as long as it is a bijective mapping and the probability, pr(T), of the occurrence of the event q∈Fr(T) still is given by $$pr(T) = \frac{|Fr(T)|}{n!}$$

Notice that pr(T) is the probability of 2 occurrences of the structured cluster T. Thus, it can be seen that the probability of K>1 occurrences of the structured cluster is $$pr(T,K)=pr(T)^{K-1}.$$

FIG. 8 illustrates evaluating Pa(•), S(•, •), and Nst'(•) functions using dynamic programming in accordance with an exemplary embodiment. FIG. 8 shows three arrays, arrays 802, 804 and 806, which store the values of the functions Pa(•), S(•, •), and Nst'(•). Array 802 stores the values for function Pa(•). Array 804 stores the values for function S(•, •). Array 806 stores the values for function Nst'(•).

The order in which the different functions are evaluated and stored in the arrays in a dynamic programming approach is illustrated in the four depicted phases. The check mark indicates that the function has been evaluated at this point. Dynamic programming is an algorithmic technique or method of solving problems exhibiting the properties of overlapping subproblems. A problem is said to have overlapping subproblems if the problem can be broken down into subproblems that are reused several times.

The word programming in the term dynamic programming has nothing to do with writing computer programs. Rather, a program is, instead, the plan for action that is produced. For instance, a finalized schedule of events at an exhibition is sometimes called a program. Programming, in this sense, is finding an acceptable plan of action. In other words, the term program refers to a set of rules which anyone can follow to solve a problem. The set of rules do not have to be written in a computer language.

It should be understood that while FIG. 8 is depicted showing only four phases, in a dynamic programming approach, a phase would exist for every value to be calculated. This also shows that Pa(•) can be computed in $O(k^2)$ time and space.

Figure 9:
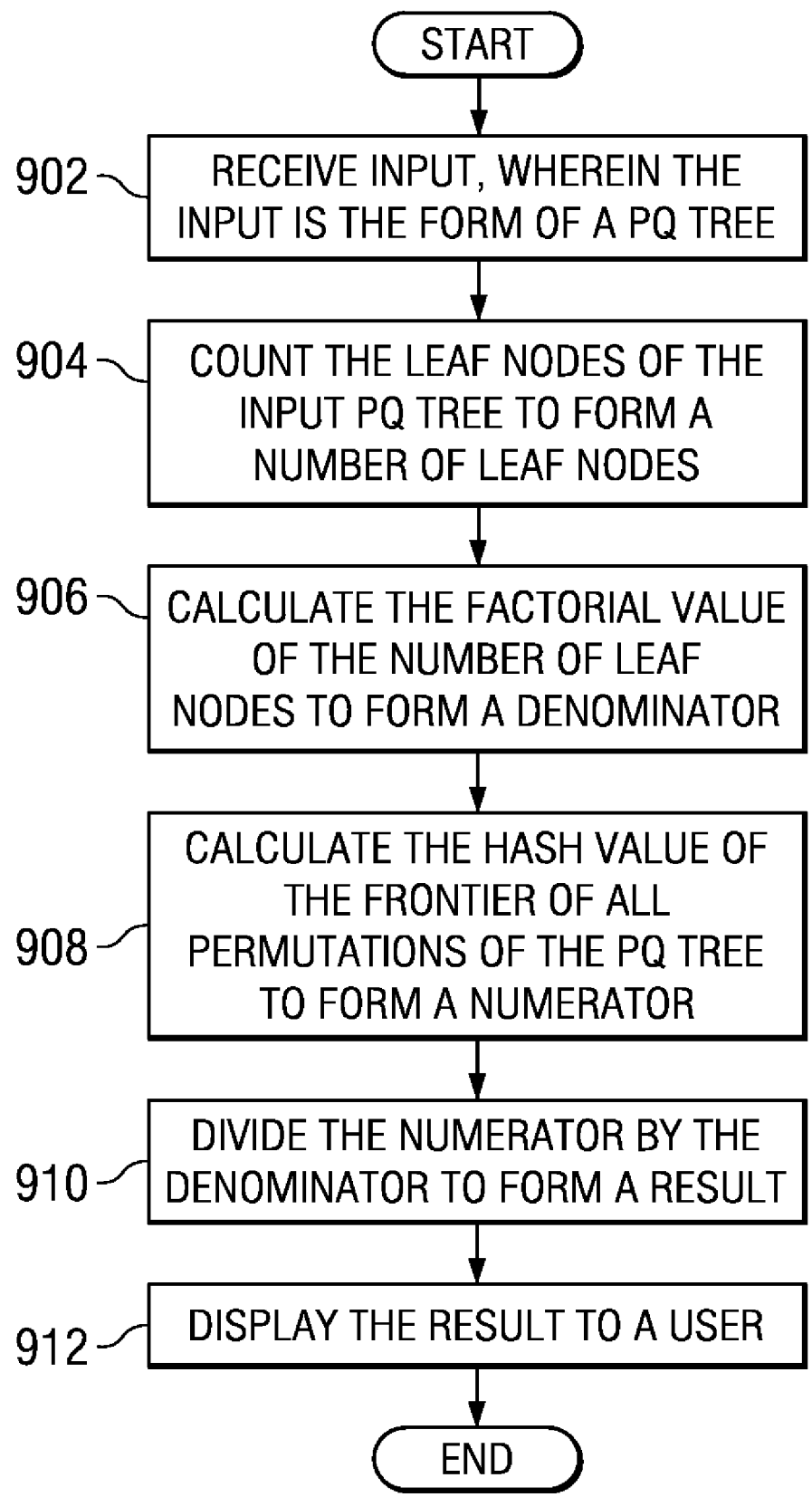
FIG. 9 is a flowchart illustrating the operation of computing the probability of occurrence of a cluster in accordance with an exemplary embodiment.

FIG. 9 is a flowchart illustrating the operation of computing the probability of occurrence of a cluster in accordance with an exemplary embodiment. The operation of FIG. 9 may be implemented in a data processing system, such as data processing 200 of FIG. 2. The operation begins when an input is received, wherein the input is the form of a PQ tree (step 902). In an alternate embodiment, the input is a structured cluster that is then converted into a PQ tree. The leaf nodes of the input PQ tree are counted to form a number of leaf nodes (step 904). The factorial value of the number of leaf nodes is calculated to form a denominator (step 906). A denominator is the number or mathematical expression, except for zero, below the line in a common fraction. A denominator is the devisor of a numerator. A numerator is the number or mathematical expression written above the line in a common fraction. The hash value of the frontier of all permutations of the PQ tree is calculated to form a numerator (step 908). The numerator is divided by the denominator to form a result (step 910). The result is displayed to user (step 912) and the operation ends. In an alternate embodiment, the result is stored in non-volatile memory.

Thus, exemplary embodiments provide a solution to computing the probability of occurrence of a structured cluster in the form of a PQ tree T by computing the size of |Fr(T)| exactly. This is a better estimate of the probability of clusters of objects, such as genes, than the ones that ignore the internal sub-clusters. Exemplary embodiments also provide for counting, as well as enumerating, exactly the number of permutations of a cluster that do not contain any non-trivial intervals, which are called P-arrangements.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Further, a computer storage medium may contain or store a computer readable program code such that when the computer readable program code is executed on a computer, the execution of this computer readable program code causes the computer to transmit another computer readable program code over a communications link. This communications link may use a medium that is, for example without limitation, physical or wireless.

A data processing system suitable for storing and/or executing program code will include at least one processor coupled directly or indirectly to memory elements through a system bus. The memory elements can include local memory employed during actual execution of the program code, bulk storage, and cache memories, which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for computing the probability of occurrence of a cluster, the computer implemented method comprising:
    receiving an input, wherein the input comprises a PQ tree;
    counting leaf nodes of the PQ tree to form a number of leaf nodes;
    calculating, using a processor, a factorial value of the number of leaf nodes to form a denominator;
    calculating a hash value of a frontier of all permutations of the PQ tree to form a numerator;
    determining a ratio of the numerator to the denominator to form a result; and
    displaying the result to a user.

2. The computer implemented method of claim 1, wherein the input comprises:
    a structured cluster; and
    converting the structured cluster to the PQ tree.

3. The computer implemented method of claim 1, wherein the result is a probability of an occurrence of a cluster, given individual probabilities of genes.

4. The computer implemented method of claim 1, wherein calculating the hash of hash value of a frontier of all permutations of the PQ tree comprises:
    inverse-telescoping a first arrangement with a second arrangement by replacing an element out of a plurality of elements of the first arrangement with the second arrangement and renumbering specific elements of the plurality of elements of the first arrangement, forming a new arrangement.

5. The computer implemented method of claim 4, wherein the second arrangement is a P-arrangement.

6. The computer implemented method of claim 5, wherein the specific elements are elements in the first arrangement that occur after the element that was replaced by the second arrangement and wherein the specific elements are renumbered by increasing the specific elements by a value of one less than a value of a size of the second arrangement.

7. The computer implemented method of claim 5, wherein the specific elements are elements in the first arrangement that occur before the element that was replaced by the second arrangement and wherein the specific elements are renumbered by decreasing the specific elements by a value of one less than a value of a size of the second arrangement; and
    increasing all the elements of the new arrangements by a specific value in order to cause all the elements of the new arrangement to be positive integers, wherein the specific value equals the value needed to increase the lowest integer in the new arrangement to one.

8. A computer program product comprising:
    a computer readable storage device having computer usable program code for computing the probability of occurrence of a cluster, the computer program product comprising:
    computer usable program code for receiving an input, wherein the input comprises a PQ tree;
    computer usable program code for counting leaf nodes of the PQ tree to form a number of leaf nodes;
    computer usable program code for calculating a factorial value of the number of leaf nodes to form a denominator;
    computer usable program code for calculating a hash value of a frontier of all permutations of the PQ tree to form a numerator;
    computer usable program code for determining a ratio of the numerator to the denominator to form a result; and
    computer usable program code for displaying the result to a user.

9. The computer program product of claim 8, wherein the input comprises:
    a structured cluster; and
    computer usable program code for converting the structured cluster to the PQ tree.

10. The computer program product of claim 8, wherein the result is a probability of an occurrence of a cluster, given individual probabilities of genes.

11. The computer program product of claim 8, wherein the computer usable program code for calculating the hash of hash value of a frontier of all permutations of the PQ tree comprises:
    computer usable program code for inverse-telescoping a first arrangement with a second arrangement by replacing an element out of a plurality of elements of the first arrangement with the second arrangement and renumbering specific elements of the plurality of elements of the first arrangement, forming a new arrangement.

12. The computer program product of claim 11, wherein the second arrangement is a P-arrangement.

13. The computer program product of claim 12, wherein the specific elements are elements in the first arrangement that occur after the element that was replaced by the second arrangement and wherein the specific elements are renumbered by increasing the specific elements by a value of one less than a value of a size of the second arrangement.

14. The computer program product of claim 12, wherein the specific elements are elements in the first arrangement that occur before the element that was replaced by the second arrangement and wherein the specific elements are renumbered by decreasing the specific elements by a value of one less than a value of a size of the second arrangement; and
    computer usable program code for increasing all the elements of the new arrangements by a specific value in order to cause all the elements of the new arrangement to be positive integers, wherein the specific value equals the value needed to increase the lowest integer in the new arrangement to one.

15. A data processing system for computing the probability of occurrence of a cluster, the data processing system comprising:
a bus;
a communications unit connected to the bus;
a storage device connected to the bus, wherein the storage device includes computer usable program code; and
a processor unit connected to the bus, wherein the processor unit executes the computer usable program code to receive an input, wherein the input comprises a PQ tree; count leaf nodes of the PQ tree to form a number of leaf nodes; calculate a factorial value of the number of leaf nodes to form a denominator; calculate a hash value of a frontier of all permutations of the PQ tree to form a numerator; determine a ratio of the numerator to the denominator to form a result; and display the result to a user.

16. The data processing system of claim 15, wherein the input comprises:
a structured cluster; and
wherein the processor unit further executes the computer usable program code to convert the structured cluster to the PQ tree.

17. The data processing system of claim 15, wherein the result is a probability of an occurrence of a cluster, given individual probabilities of genes.

18. The data processing system of claim 15, wherein the processor unit executing the computer usable program code to calculate the hash of hash value of a frontier of all permutations of the PQ tree comprises:
the processor unit executing the computer usable program code to inverse-telescope a first arrangement with a second arrangement by replacing an element out of a plurality of elements of the first arrangement with the second arrangement and renumbering specific elements of the plurality of elements of the first arrangement, forming a new arrangement.

19. The data processing system of claim 18, wherein the second arrangement is a P-arrangement.

20. The data processing system of claim 19, wherein the specific elements are elements in the first arrangement that occur after the element that was replaced by the second arrangement and wherein the specific elements are renumbered by increasing the specific elements by a value of one less than a value of a size of the second arrangement.

* * * * *